United States Patent [19]
Raff

[11] Patent Number: 5,971,931
[45] Date of Patent: Oct. 26, 1999

[54] BIOLOGIC MICROMONITORING METHODS AND SYSTEMS

[76] Inventor: Gilbert Lewis Raff, 1221 Rockrose Rd., N.E., Albuquerque, N.Mex. 87122

[21] Appl. No.: 08/219,716

[22] Filed: Mar. 29, 1994

[51] Int. Cl.$^6$ .................................. A61B 5/02; A61B 5/04
[52] U.S. Cl. .............................................................. 600/485
[58] Field of Search ..................................... 128/670, 673, 128/687, 691, 692, 672, 677, 680, 679, 689, 690; 364/413.01, 413.02, 413.03; 600/485

[56] References Cited

U.S. PATENT DOCUMENTS

| | | | |
|---|---|---|---|
| 3,658,054 | 4/1972 | Iberall | 128/672 |
| 3,704,708 | 12/1972 | Iberall | 128/680 |
| 3,815,583 | 6/1974 | Scheidt | 128/666 |
| 3,972,320 | 8/1976 | Kalman | 128/706 |
| 4,172,450 | 10/1979 | Rogers et al. | 128/679 |
| 4,269,193 | 5/1981 | Eckerle | 128/672 |
| 4,301,808 | 11/1981 | Taus | 128/687 |
| 4,651,750 | 3/1987 | Northeved | 128/736 |
| 4,869,261 | 9/1989 | Penaz | 128/667 |
| 4,875,477 | 10/1989 | Waschke et al. | 128/206.21 |
| 4,952,928 | 8/1990 | Carroll et al. | 340/825.54 |
| 5,064,410 | 11/1991 | Frenkel et al. | 600/26 |
| 5,158,091 | 10/1992 | Butterfield et al. | 128/672 |
| 5,230,342 | 7/1993 | Bobo, Jr. et al. | 128/677 |
| 5,319,185 | 6/1994 | Obata | 235/472 |
| 5,333,622 | 8/1994 | Casali et al. | 128/864 |
| 5,335,664 | 8/1994 | Nagashima | 128/696 |
| 5,339,818 | 8/1994 | Baker et al. | 128/677 |

OTHER PUBLICATIONS

*Dorland's Pocket Medical Dictionary*; (c) 1989 by W. B. Saunders Company; pp. 48, 49, 56, 57, 62, 63, 68, 69, 486 and 487.

*Primary Examiner*—Stephen R. Tkacs
*Attorney, Agent, or Firm*—Neal Kalishman

[57] ABSTRACT

Methods and systems for monitoring biologic conditions including microsensors, wireless telemetry, expert systems, monitoring stations, and communication abilities. The methods and systems of the invention allow for patient monitoring and analysis at remote locations utilizing wireless telemetry.

50 Claims, 6 Drawing Sheets

Fig. 2
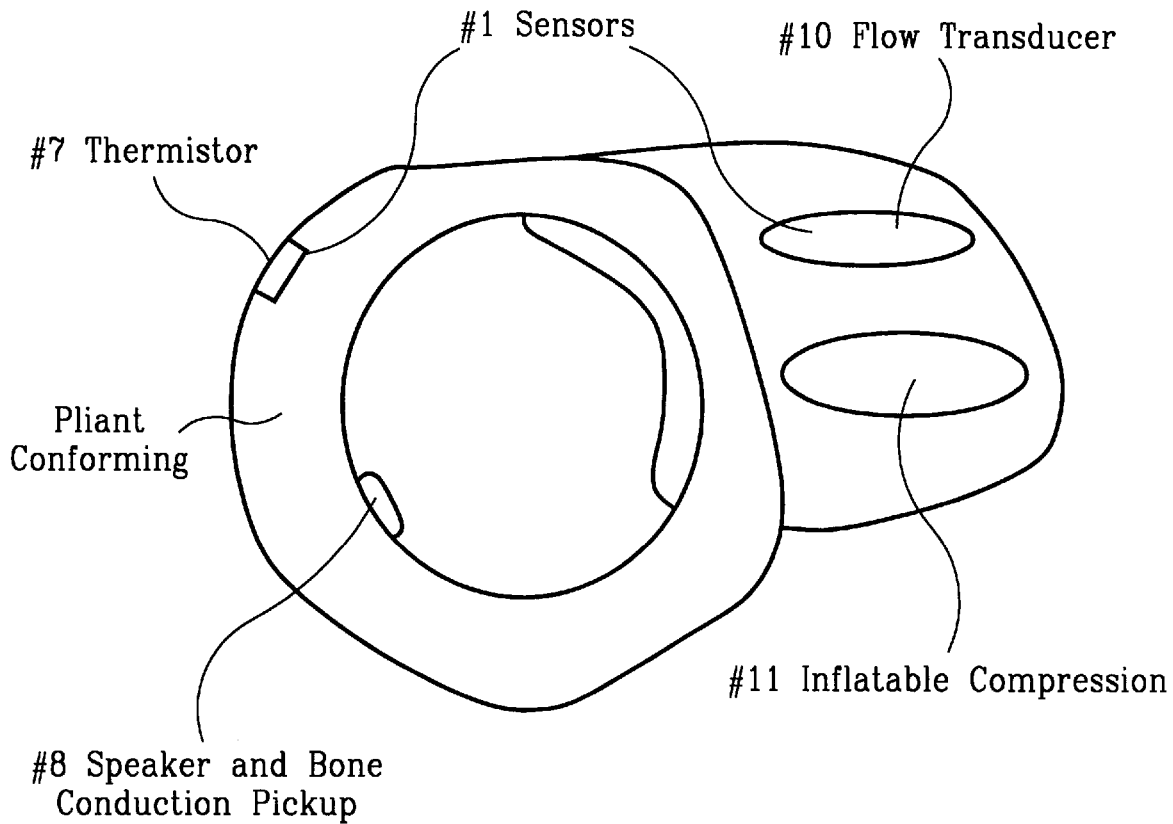
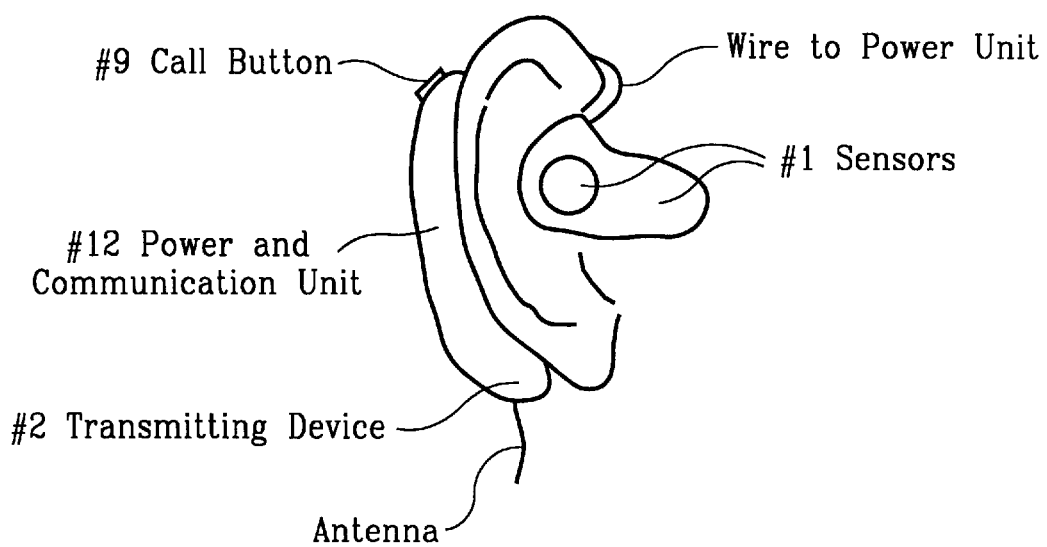

Fig. 3
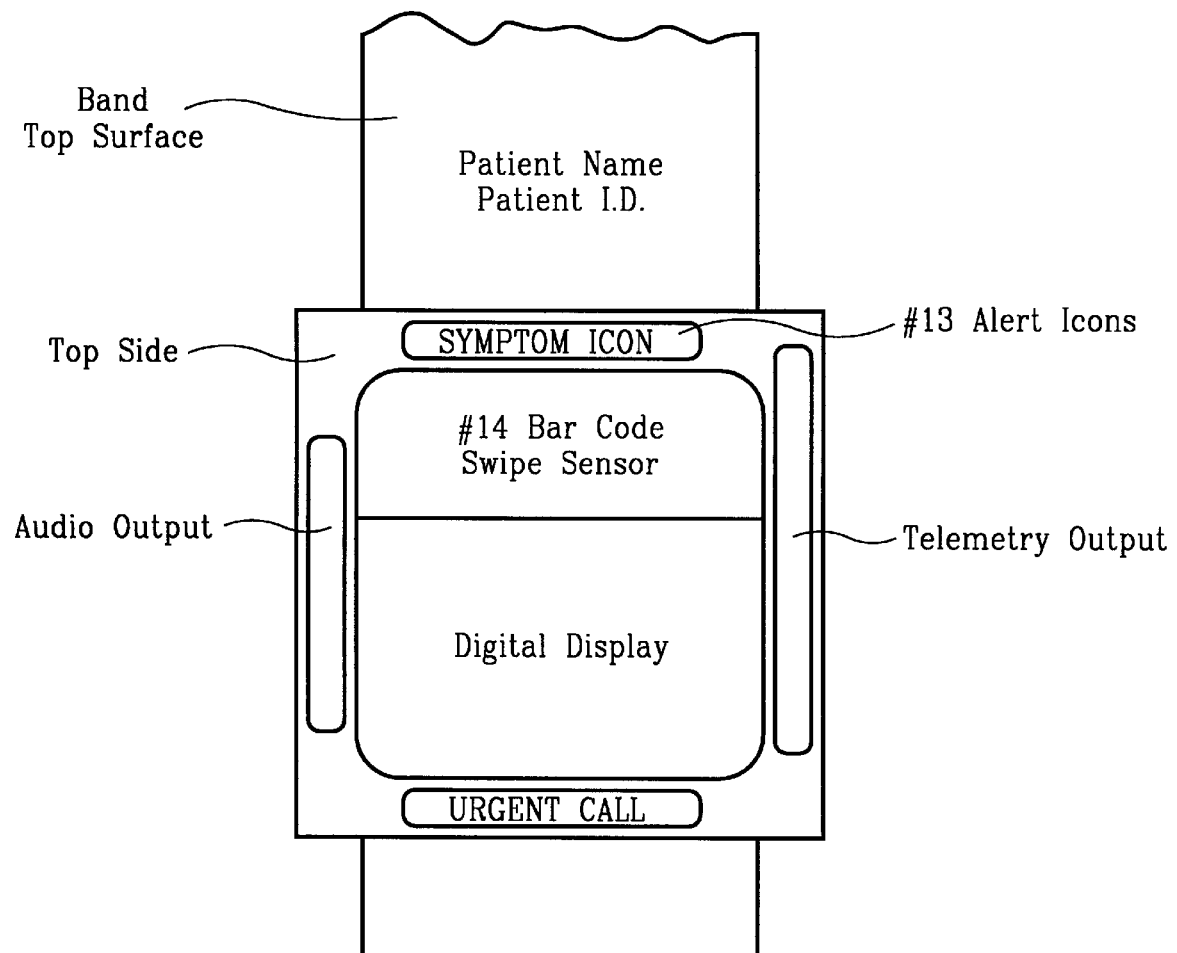
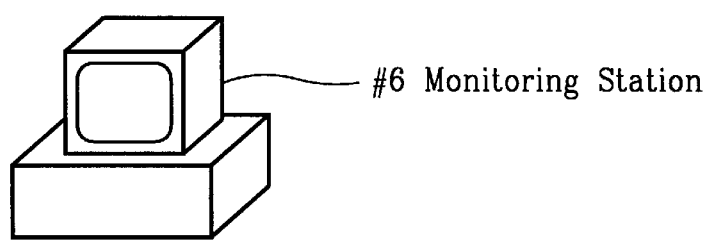

Fig. 6
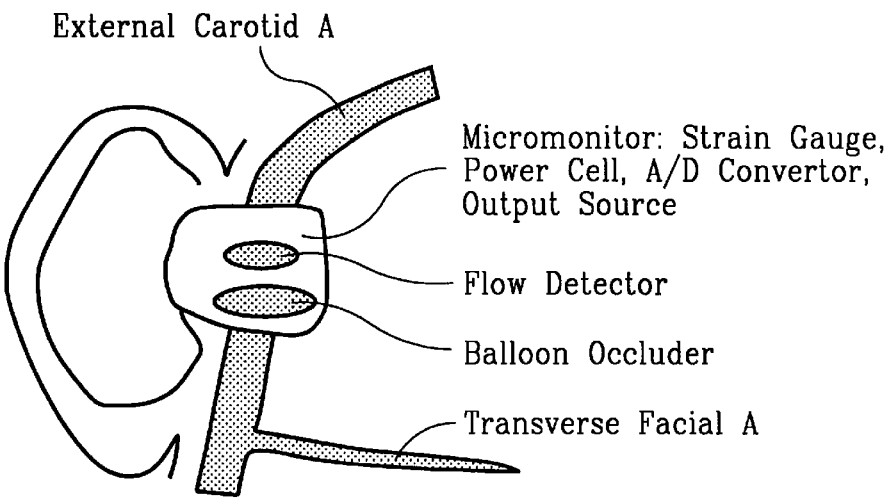
Device Output
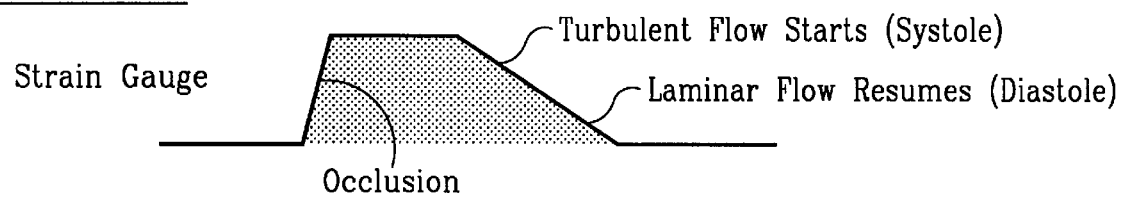
Device Configuration: Samples
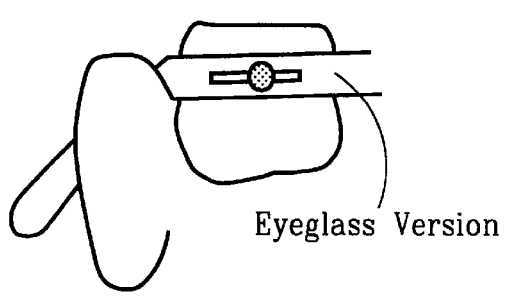
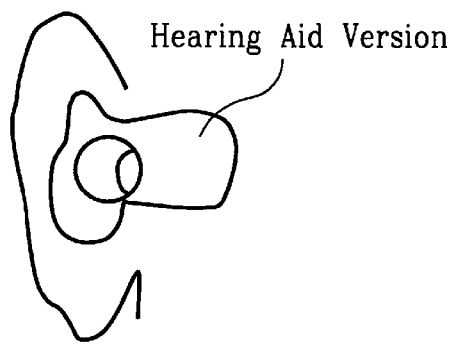

BIOLOGIC MICROMONITORING METHODS AND SYSTEMS

FIELD OF THE INVENTION

The invention relates to monitoring biologic conditions and administration of drugs remotely. More particularly, the invention relates to the use of micromonitoring sensors which transmit data either directly to a platform for analysis and/or retransmission wirelessly to a monitoring station.

BACKGROUND OF THE INVENTION

Measuring, monitoring and recording of biological and environmental conditions are important in maintaining wellness and treatment. In a hospital environment the pulse rate, respiratory rate, temperature, and blood pressure are taken and recorded on a regular basis. These measurements are referred to as vital signs. In rare cases the sensors are attached to the patient and the data is transmitted to the nurse's station. Such transmitting units are usually bulky and in all cases require hard wiring.

The same is true of outpatient monitoring. Bulky equipment is required which restricts the patients mobility. The patient is restricted to a limited area. One of the problems in developing a micromonitoring system has been the inability to monitor blood pressure separately from the other vital signs in a miniature low energy device that is accurate in ambulatory patients.

EKG monitoring is another area of key importance. Sudden cardiac death remains one of the major causes of death in the U.S. One of the barriers to prevention of this common event is the inability of many people to sense pain or discomfort during cardiac injury. Death can be avoided with proper intervention if injury can be detected in these individuals.

Monitoring of blood pool and cellular elements can be very valuable in monitoring and treating of vascular, neurologic, hematopoetic, biochemical and immunologic body functions. Such monitoring is now performed by conventional radiological, diagnostic, and interventional techniques.

Many environmental and biological hazards are currently measured only after a badge collects data over a period of days or weeks, not continuously during exposure. Injuries may be prevented if exposure could be determined continuously, and the monitored individual alerted right away.

SUMMARY OF THE INVENTION

A biologic micromonitoring system for measuring medical information and administering therapy which comprises: A) An ear piece that has sensors for the vital signs including blood pressure, and amplifiers and transceivers which transmit the measurement from the ear piece to a wearable platform; B) A wearable receiving platform with transceiving and display capabilities; C) A monitoring station including data display, computing, software including expert system anomaly recognition, alarm signal transceiving to ear device and healthcare team; D) EKG sensors which transmit to the platform; E) An eye piece with spectrophotometric sensing that can detect biochemical information from the retina and transmit to the platform; F) An implanted subcutaneous syringe that can inject drugs at the instruction of the platform, and be monitored by the eye piece; G) Environmental sensors which can transmit to the platform.

BRIEF DESCRIPTION OF THE DRAWINGS

FIG. 2 illustrates the ear piece of the invention.

FIG. 3 illustrates the receiving platform of the invention.

FIG. 6 illustrates method of measuring of blood pressure.

DESCRIPTION OF THE INVENTION

Figure 1:
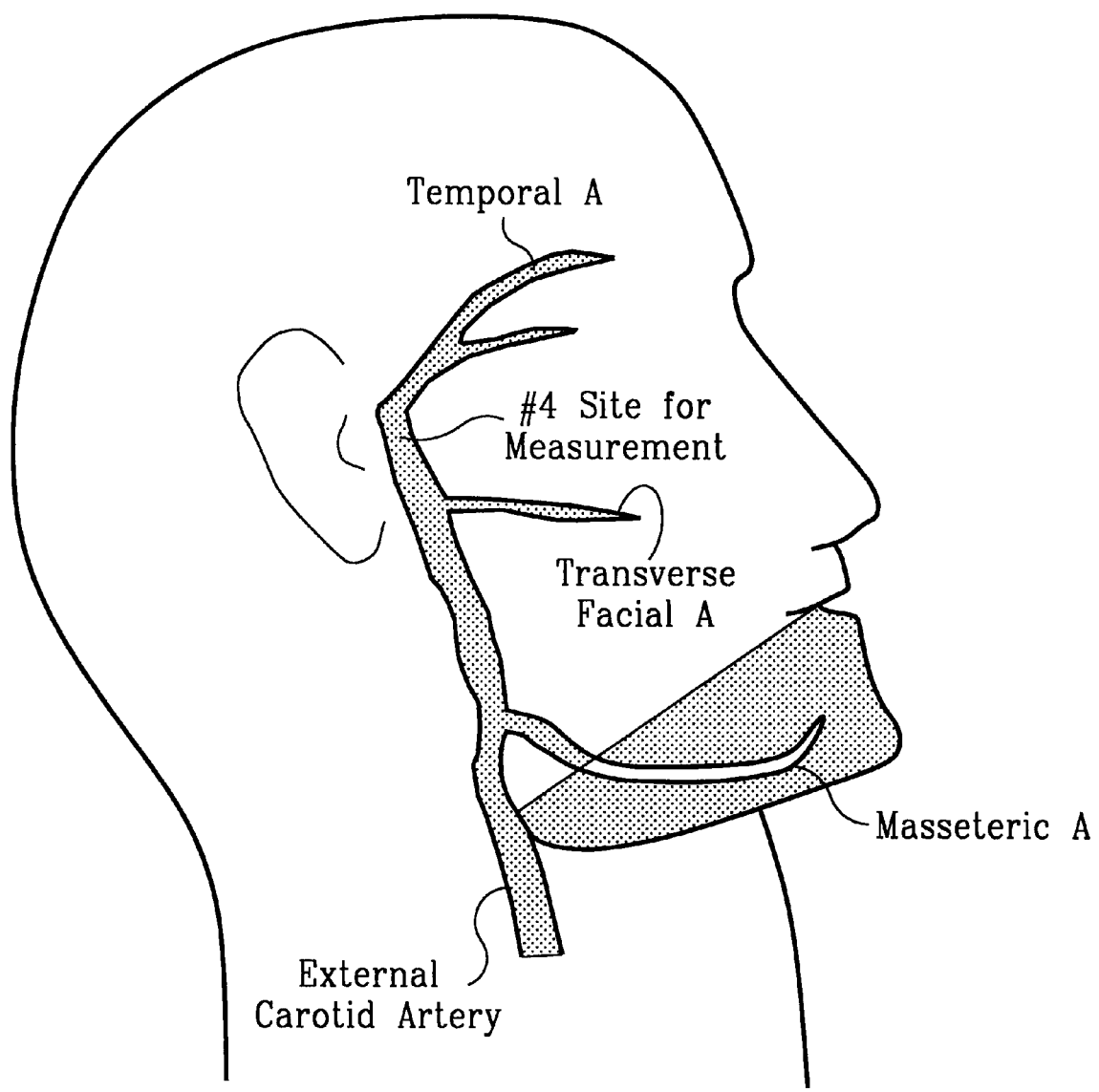
FIG. 1 illustrates the site of monitoring of blood pressure, pulse and respiratory rate.

The basic monitoring system comprises microsensors (FIG. 2, #1), a transmitting device (FIG. 2, #2), a platform device (FIG. 3, #3), and a monitoring station (FIG. 3, #6). With respect to monitoring vital signs the sensor is located in and around the ear. Temperature is the only vital sign which is commonly measured at this site. However, it has been found that blood pressure, heart rate and respiration can be measured by compressing the preauricular section of the external carotid artery (FIG. 1, #4), and monitoring the waveform of flow distally (FIG. 6, #5). A monitoring station includes signal transceiving, amplification, data display, and expert system software response.

The method involves measuring blood pressure from compression and decompression of the External Carotid Artery on the preauricular area including the Tragal Branch of that artery, with downstream measurement of flow waveforms. Heart rate is measured from the same waveform, from peak to peak measurement of that sinusoidal waveform. Respiratory rate is measured as peak to peak variation in amplitude of sinusoidal flow during noncompressed periods. Oximetry is measured using reflectance infrared spectrophotometry from the same arterial branch. Temperature is measured by thermocouple (FIG. 2, #7) from the external ear canal. Oral communication is accomplished from external ear canal using a speaker and bone conduction pickup (FIG. 2, #8) to facilitate communication between the nursing station and the patient. Transmission from battery powered device, signals to computer is done via amplified wireless interconnection. Interactive recalibration is used to rebalance sensors remotely on a programmed schedule. Distress or request call from patient to care team is done via call button on device (FIG. 2, #9). Device consists of power supply, transceiver, amplification and computing section behind ear, and sensor and compression module in and around external ear canal. Device is reusable and fitted to each patient.

The microsensor include a measuring mechanism for temperature and blood flow transducer (FIG. 2, #10), variably a doppler, infrared, or ultrasound sensor for determining pulse rate, respiratory rate, and blood pressure. The sensor has an calibrated inflatable compression section (FIG. 2, #11) which compresses the carotid artery in order to obtain blood pressure. The ear unit (FIG. 2) has a power source (FIG. 2, #12) and a transmitter (FIG. 2, #2).

The transmitter transmits the signals from the sensor either directly to a monitoring station or to a platform which is worn by the patient on the wrist. The platform (FIG. 3) has a number of features. It is able to receive the signal from the transmitter. It is able to analyze the signal and provide an appropriate display on screen. It can send the signal through retransmitter to the monitoring station (FIG. 3, #6).

Both the ear piece and the platform can provide voice communications to trained staff. Data communications can be used to instruct the sensors to perform recalibration tests. Also, the patient can be contacted regarding symptoms and appropriate instructions issued and tests performed. Certain icons on the face of the platform (FIG. 3, #13) can alert the wearer to various dangerous conditions. Further, the platform can have a bar code reader (FIG. 3, #14). The microprocessor in the platform can be programmed to accept bar codes from prescription medicines or procedures. If the patient either runs the wrong medicine or does not at the appropriate time run a medicine over the bar code reader, the platform will so notify both the patient and the monitoring station. In many situations, the wrist platform can serve as an independent monitoring unit.

Figure 5:
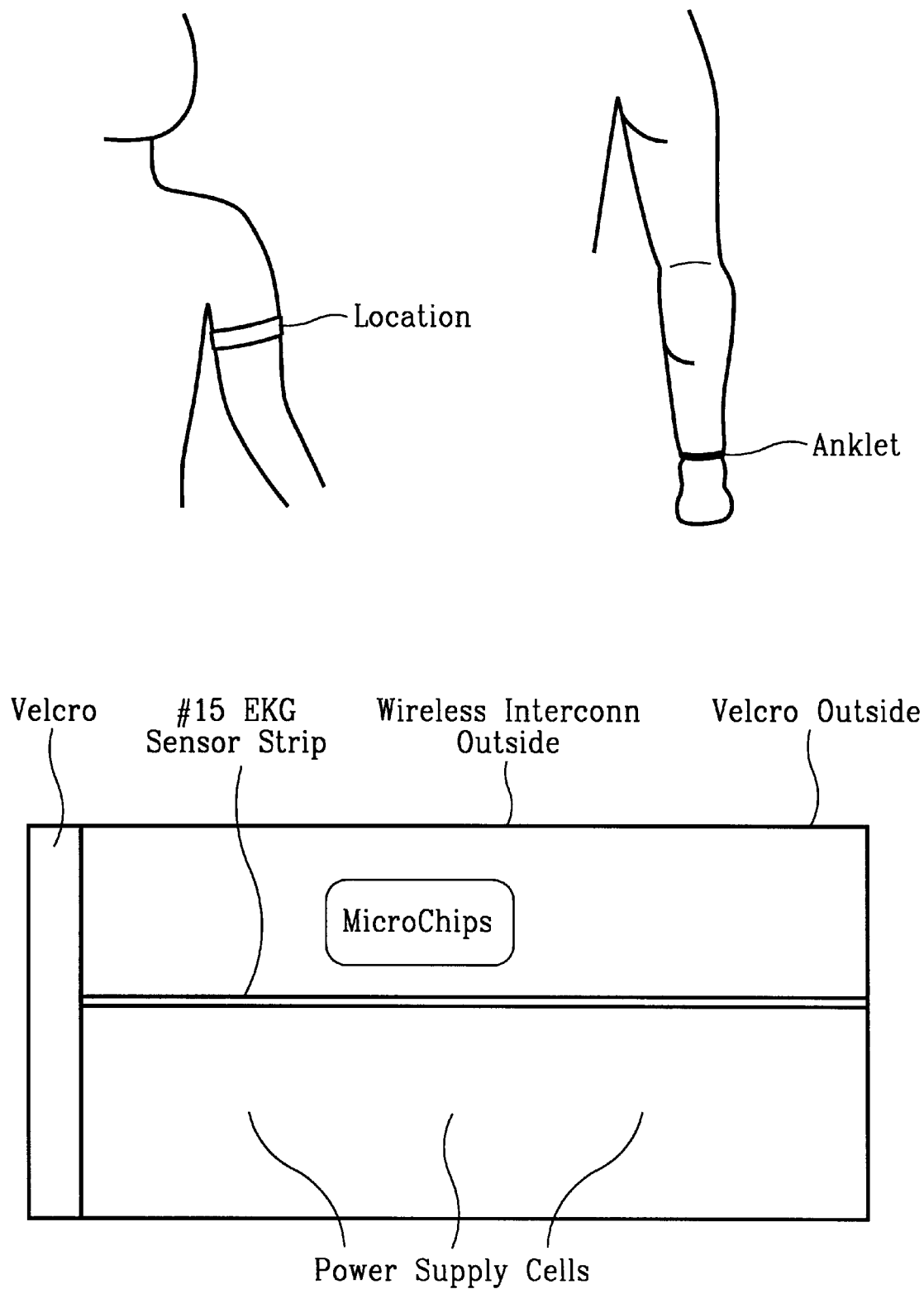
FIG. 5 illustrates the EKG sensor strip of the invention.

As shown in FIG. 5, (#15) an EKG sensor can be used in place of or along with the vital signs sensor. It can either communicate directly to the monitoring station or to the platform for retransmission to the monitoring station. Similarly environmental sensors, such as radiation detectors, can be included or substituted for the illustrated sensors.

Figure 4:
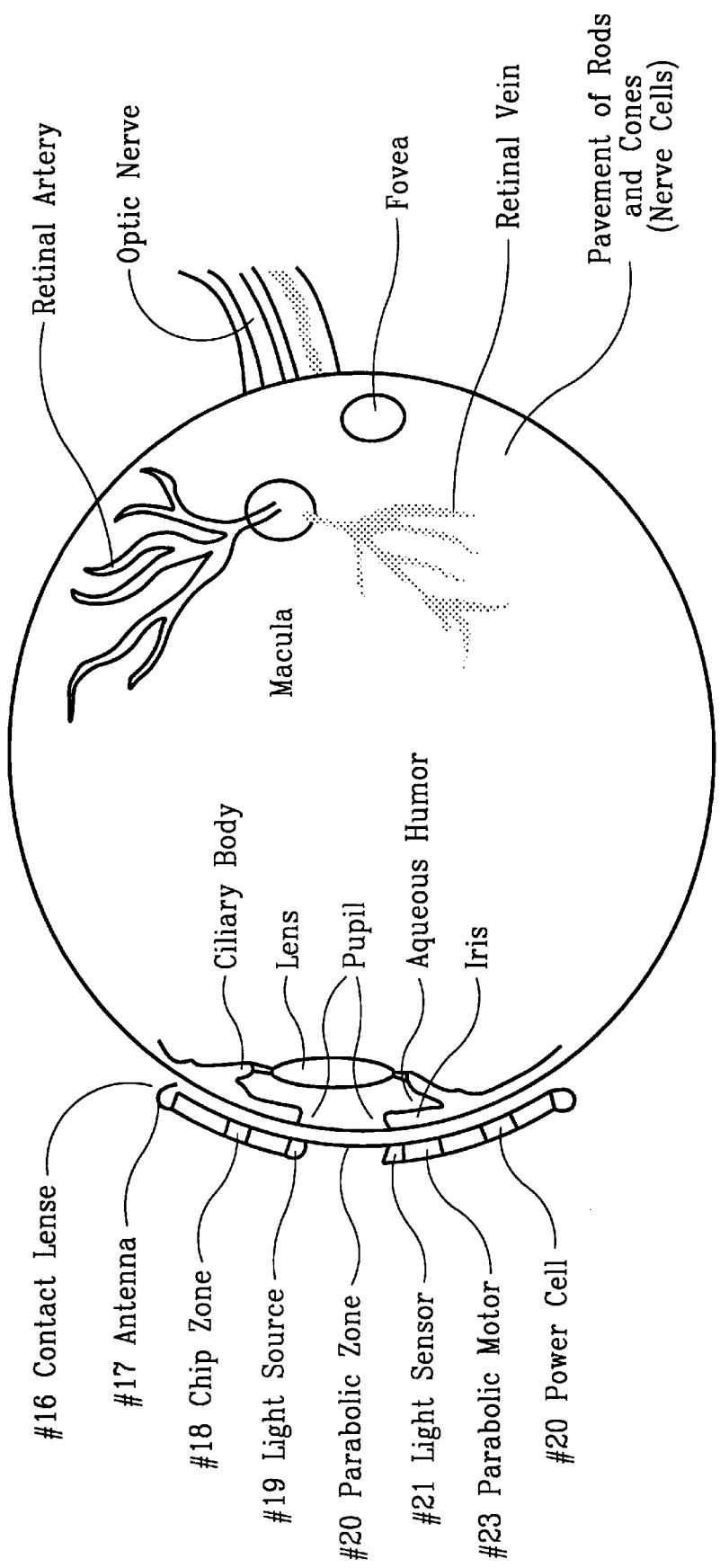
FIG. 4 illustrates the eye piece of the invention located on an eye.

The platform can also communicate with a special eye piece (FIG. 4, #16). The eye piece contains a transmitter #17, a microchip #18, a light source #19, a power cell #20, a light sensor #21, a parabolic mirror #22, and a parabolic motor #23. Light is generated by the light source, reflected off the semi-silvered inner parabolic mirror with aiming by the parabolic motor towards the macula, and is further directed by the eye's lens towards the foveal area. The reflected light is received by sensors ringing the pupillary zone, and analyzed by the microchip. The microchip and transmitter are powered by a battery and are in communication with the platform. Through the platform (FIG. #3) information from the lens can be displayed and/or further transmitted to the monitoring station. Additionally but not illustrated, an eyeglass configuration would be employed by eyeglass wearers needing similar monitoring.

An implantable subcutaneous drug syringe can be controlled by wireless commands from the platform. The device is meant to be placed under sterile conditions using local anesthesia. It contains a reusable drug reservoir, a pump and subcutaneous nozzle, and a sealed electronic control unit has wireless reception from the platform. The platform can send programmed directions to the syringe to control the amount of infused drug and provide remote feedback and confirmation to the system of the administration of the drug as directed.

The microchip or the platform can control drug reservoirs based on readings obtained on using appropriate wavelengths of light. Spectrophotometric data can be retrieved from the highly vascular retinal surface. Since the iris is opaque, a duplicate iris facade can cloak the electronic machinery beneath. Using a partially reflectant central glass zone over the pupil the wearer will be able to see, yet the inner parabolic surface of the lens (FIG. 4, #22) can focus a generated light source on the retina.

Communication between the platform or sensor and the monitoring station can occur in a number of different ways. These technologies include satellite, cellular, interactive systems, and personal communications systems. The system is wireless either from the sensor, if it has direct transmitting capabilities, or the platform to either a retransmitter or to the monitoring station. The monitoring, if the patient is within a hospital, will normally be at a nurses station. If the patient is not hospitalized then the monitoring will be at a hospital, central station or doctor's office. With this system a patient can be monitored world wide.

I claim:

1. A biological micromonitoring system for monitoring vital signs in humans which comprises a structure for holding against the head at least one sensor which measured blood pressure and is positioned at the preauricular portion of the external carotid artery.

2. The system of claim 1 wherein said structure further comprises at least one sensor for measuring temperature.

3. The system of claim 2 wherein said temperature sensor is located within the ear.

4. The system of claim 1 wherein said structure further comprises at least one sensor for measuring pulse.

5. The system of claim 1 wherein said structure further comprises at least one sensor for measuring respiratory rate.

6. The system of claim 1 wherein said structure further comprises a transmitter which transmits data from said sensors.

7. The system of claim 6 wherein said transmitter is wireless.

8. The system of claim 7 wherein said transmitter transmits data to a platform.

9. The system of claim 8 wherein said platform further comprises a visual display.

10. The system of claim 8 wherein said system further comprises a monitoring station for receipt of data from said platform.

11. The system of claim 8 wherein said platform further comprises a bar code reader for imputing data into said platform.

12. The system of claim 7 wherein said system further comprises a monitoring station for receipt of data from said transmitter.

13. The system of claim 6 wherein said transmitter transmits data to a platform.

14. The system of claim 13 wherein said platform further comprises a visual display.

15. The system of claim 13 wherein said system further comprises a monitoring station for receipt of data from said platform.

16. The system of claim 13 wherein said platform further comprises a bar code reader.

17. The system of claim 6 wherein said system further comprises a monitoring station for receipt of data from said transmitter.

18. The system of claim 1 wherein said system further comprises an EKG sensor system.

19. The system of claim 18 wherein said EKG sensor system further comprises a transmitter.

20. The system of claim 1 wherein said system further comprises a compression device for compressing the external carotid artery.

21. The system of claim 1 wherein said structure is contained in an ear piece.

22. The system of claim 1 wherein said structure is mounted on a frame that goes from one side of the head to the other side of the head.

23. A biological micromonitoring system that monitors vital signs in humans that comprises a frame having microsensors that measure at least two different vital signs, one of which being blood pressure, wherein said frame holds a microsensor for measuring the blood pressure against head at the preauricular portion of the external carotid artery.

24. The system of claim 23 wherein at least one of the vital signs measured is temperature.

25. The system of claim 23 wherein at least one of the vital signs measured is pulse.

26. The system of claim 23 wherein at least one of the vital signs measured is respiratory rate.

27. The system of claim 23 wherein said frame further comprises a transmitter.

28. The system of claim 27 wherein said transmitter is wireless.

29. The system of claim 27 wherein said system further comprises a platform for receiving data from said frame.

30. The system of claim 29 wherein said platform further comprises a transmitter.

31. The system of claim 30 wherein said system further comprises a monitoring station for receiving data from said platform.

32. The system of claim 29 wherein said platform further comprises bar code reader for imputting information into said platform.

33. The system of claim 29 wherein said platform further comprises a visual display that displays data received from said microsensors.

34. The system of claim 27 wherein said system further comprises a monitoring station for receiving data from said frame.

35. The system of claim 23 wherein the system further comprises an EKG sensor system.

36. The system of claim 23 wherein the frame goes from one side of the head to the other side of the head.

37. The system of claim 23 wherein at least a portion of the frame contains an ear piece.

38. A method of monitoring human vital signs which comprises placing a sensor that measures blood pressure on the head at to the preauricular portion of the external carotid artery and transmitting the measurements from said sensor.

39. The method of claim 38 which further comprises placing a sensor in the ear to measure temperature.

40. The method of claim 38 which further comprises using sensors on the head to measure pulse.

41. The method of claim 38 which further comprises using sensors on the head to measure respiratory rate.

42. The method of claim 38 wherein said data is transmitted to a platform.

43. The method of claim 42 wherein said transmission is wireless.

44. The method of claim 42 wherein said platform has a bar code reader for capturing information regarding the administration of drugs and procedures.

45. The method of claim 42 wherein said platform transmits data to a monitoring station.

46. The method of claim 45 wherein said transmission is wireless.

47. The method of claim 38 wherein said data is transmitted to a monitoring station.

48. The method of claim 47 wherein said transmission is wireless.

49. The method of claim 38 wherein the sensor is placed on an ear piece.

50. The method of claim 38 wherein the sensor is mounted on a frame that goes from one side of the head to the other side of the head.

* * * * *